(12) United States Patent
Chan

(10) Patent No.: US 9,645,112 B2
(45) Date of Patent: May 9, 2017

(54) AUTO-CLEANING AND AUTO-ZEROING SYSTEM USED WITH A PHOTO-IONIZATION DETECTOR

(75) Inventor: Wai Hoe Chan, Singapore (SG)

(73) Assignee: R2CD Holdings Pte Ltd., Singapore (SG)

( * ) Notice: Subject to any disclaimer, the term of this patent is extended or adjusted under 35 U.S.C. 154(b) by 1285 days.

(21) Appl. No.: 13/512,400

(22) PCT Filed: Jan. 19, 2010

(86) PCT No.: PCT/SG2010/000014
§ 371 (c)(1),
(2), (4) Date: May 29, 2012

(87) PCT Pub. No.: WO2011/090433
PCT Pub. Date: Jul. 28, 2011

(65) Prior Publication Data
US 2012/0252347 A1    Oct. 4, 2012

(51) Int. Cl.
*F24F 7/06* (2006.01)
*G01N 27/64* (2006.01)
*G01N 27/68* (2006.01)

(52) U.S. Cl.
CPC ............. *G01N 27/64* (2013.01); *G01N 27/68* (2013.01)

(58) Field of Classification Search
CPC ...................................................... G01N 27/64
(Continued)

(56) References Cited

U.S. PATENT DOCUMENTS 3,933,432 A * 1/1976 Driscoll ..................... 436/100
4,904,282 A * 2/1990 Stuble et al. ................. 95/20
(Continued)

FOREIGN PATENT DOCUMENTS

| JP | 2-68108 A | 3/1990 |
| RU | 2293311 C1 | 2/2007 |
| WO | 98/26387 A2 | 6/1998 |

OTHER PUBLICATIONS

International Search Report and Written Opinion dated Feb. 26, 2010 in corresponding PCT application No. PCT/SG2010/000014, 8 pages.
(Continued)

*Primary Examiner* — Gregory Huson
*Assistant Examiner* — Martha Becton
(74) *Attorney, Agent, or Firm* — Nields, Lemack & Frame, LLC

(57) ABSTRACT

An auto-cleaning and auto-zeroing system (1) comprises a first conduit for flow of ambient gas (16) and a $2^{nd}$ conduit (22) for flow of ambient air (18). A cleaning chamber (12) removes impurities from ambient air (18). The $1^{st}$ conduit (20) and $2^{nd}$ conduit (22) are connected to a valve, operated by the continuous motor, which continuously draws ambient gas (16) or cleaned and filtered ambient air (18) through the system. Cleaned and filtered ambient air (18) enters the ionization chamber (10) to carry out a cleaning (flushing) and a cleaning (ionization) cycle. In this manner, contaminants and pollutants left in the ionization chamber (10) from the measurement of ambient gas (16) are flushed out and removed.

25 Claims, 8 Drawing Sheets

(58) Field of Classification Search
USPC .......................................................... 454/338
See application file for complete search history.

(56) References Cited

U.S. PATENT DOCUMENTS

| | | | | |
|---|---|---|---|---|
| 5,240,018 | A * | 8/1993 | Clark ...................... | C23G 5/04 134/105 |
| H001337 | H * | 7/1994 | Hoeppel ..................... | 435/300.1 |
| 5,610,835 | A * | 3/1997 | Dominguez ........... | G01N 30/62 436/161 |
| 5,723,861 | A * | 3/1998 | Carnahan ............. | G01N 27/622 250/287 |
| 5,736,739 | A * | 4/1998 | Uber .................... | G01N 27/622 250/287 |
| 5,773,833 | A * | 6/1998 | Hsi ........................ | G01N 27/64 250/379 |
| 6,225,633 | B1 * | 5/2001 | Sun ....................... | G01N 27/66 250/281 |
| 6,333,632 | B1 * | 12/2001 | Yang ..................... | G01N 27/70 324/459 |
| 6,734,435 | B2 * | 5/2004 | Sun et al. ................ | 250/423 P |
| 6,959,610 | B1 | 11/2005 | Bowers | |
| 6,967,485 | B1 * | 11/2005 | Hsueh .................... | G01N 27/64 250/382 |
| 7,241,989 | B2 * | 7/2007 | Miller ................. | G01N 27/622 250/281 |
| 7,302,313 | B2 * | 11/2007 | Sharp ..................... | G01N 1/26 700/275 |
| 7,511,268 | B2 * | 3/2009 | Landgraf ................ | H01J 49/40 250/281 |
| 7,704,748 | B2 * | 4/2010 | Schaeffer ............... | G01N 25/28 422/12 |
| 8,336,402 | B2 * | 12/2012 | Glezer ................. | G01N 1/2273 73/23.34 |
| 2001/0018844 | A1 * | 9/2001 | Parekh ............... | G01N 33/0006 73/1.06 |
| 2004/0089234 | A1 * | 5/2004 | Hagglund et al. ........... | 118/663 |
| 2005/0121607 | A1 * | 6/2005 | Miller ..................... | H05H 1/24 250/287 |
| 2006/0188994 | A1 * | 8/2006 | Ding ................... | B01D 65/102 436/3 |
| 2007/0184188 | A1 | 8/2007 | Kim et al. | |
| 2010/0084549 | A1 * | 4/2010 | Ermakov ........... | H01J 49/4245 250/283 |
| 2011/0156715 | A1 * | 6/2011 | Groves ................. | G01N 27/66 324/466 |
| 2012/0292495 | A1 * | 11/2012 | Hashimoto .......... | H01J 49/423 250/281 |
| 2014/0132277 | A1 * | 5/2014 | Stearns ................. | G01N 27/64 324/464 |

OTHER PUBLICATIONS

International Preliminary Report on Patentability mailed Aug. 2, 2012 in corresponding PCT application No. PCT/SG2010/000014, 6 pages.

* cited by examiner

AUTO-CLEANING AND AUTO-ZEROING SYSTEM USED WITH A PHOTO-IONIZATION DETECTOR

FIELD OF THE INVENTION

This invention relates to an auto-cleaning and auto-zeroing system used with a volatile gas detector, particularly a continuously operated Photo-Ionization Detector (PID).

DISCUSSION OF PRIOR ART

A PID as known in the art is illustrated in FIG. 1. Such devices are generally used for monitoring gases for:
Industrial hygiene and safety
Indoor air quality
Environmental contamination
Cleanroom air quality A PID uses high-energy photons, typically in the ultraviolet (UV) range, to break gas molecules into positively charged ions. A typical PID for detection of volatile gases as shown in FIG. 1 consist of an ionization chamber, an UV lamp with sufficient energy to ionize the ionizable molecule, a voltage source for the accelerating electrode, and an amplifier capable of measuring the current flow. The ionizable molecules are bombarded by high-energy photons and are ionized when these molecules absorb high energy UV light. UV light excites these molecules, resulting in temporary loss of electrons in the molecules and the formation of positively charged ions, which is represented as:

$$R + h\nu \rightarrow R^+ + e^-$$

where
R = ionizable molecule
hv = photon energy
$R^+$ = parent molecule ion
$e^-$ = electron In the ionization chamber, the R+ ion formed by the absorption of the UV photons are collected at an electrode where the current generated is proportional to the ionized species. Molecules with ionization potential below the energy of the UV source can be ionized. The current generated is therefore a measure of the analyte concentration As a stand alone detector, a PID ionizes everything which comes into the ionization chamber with an ionization energy less than or equal to the lamp output. The gas to be measured may not be pure, containing dirt particles and other gaseous materials, and such dirt particles may be ionized too. After prolonged usage of the PID device, contamination such as dirt particles, oil particles, fluxes, water particles especially during high humidity condition, and contaminants adsorbed during prolong exposure to air, often builds up inside the ionization chamber. These contaminants are attracted to the electrodes, thus settling on them. Besides settling in the ionization chamber, the PID window (UV transparent window in FIG. 1), the electrodes, these pollutants and contaminants also settle on the inner surface tubes and the inlet pipes. In turn, the accuracy of volatile gas concentration measurement is affected as these contaminants interfere with the movement and collection of the ions and electrons on the electrodes. The contamination which have settled on the window of the PID also reduces the intensity of UV light and consequently affects the accuracy of the volatile gas concentration measurement. When this happens, the user has to take the PID apart to clean the electrodes and PID window by removing the contaminants. The cleaning will also require re-calibration with a standard zero gas (usually synthetic air/nitrogen) and span calibration gas (usually 100 ppm Isobutylene gas) in order to ensure the PID is accurate when put back into operation.

There is a need for an improved PID which has an auto-cleaning and auto-zeroing capability which will thus reduce down time and offer improved productivity of the PID device.

SUMMARY OF INVENTION

A first object of the invention is an auto-cleaning and auto-zeroing system for use with a Photo-Ionization Detector (PID), the PID having a $1^{st}$ conduit for inflow of ambient gas to be measured in the ionization chamber of the PID, during a measurement cycle, the system having:
 a continuous motor to continuously operate a pump to draw ambient gas from a source of ambient gas or ambient air from the environment;
 a valve to direct flow of ambient gas or ambient air into the ionization chamber;
 a $2^{nd}$ conduit for flow of ambient air;
 a cleaning chamber which removes pollutants and contaminants in the ambient air;
characterized in that the cleaned ambient air is drawn through the ionization chamber by the continuous motor to flush out air borne contaminants and pollutants in the ionization chamber originating from the ionization of ambient gas during the measurement cycle.

Preferably, the system further have:
 a valve, which is a 4/2 valve to direct flow of ambient gas or ambient air into the ionization chamber;
 an inlet conduit leading from the 4/2 valve to the ionization chamber;
 an outflow conduit to outflow of ambient gas or ambient air from the ionization chamber;
 a splitter connector, which opens to allow or closes to prevent ambient gas or ambient air leaving from the ionization chamber through the outflow conduit;
characterized in that the cleaned ambient air is drawn by the continuous motor through the cleaning chamber into the $2^{nd}$ conduit and into the inlet conduit through operation of the 4/2 valve, and into the ionization chamber to flush out air borne contaminants and pollutants in the ionization chamber originating from the ionization of ambient gas during the measurement cycle, said air borne contaminants and pollutants leaving the ionization chamber via the outflow conduit, through the opening of the splitter connector.

Preferably, the $2^{nd}$ conduit leads from the cleaning chamber to the 4/2 valve.

More advantageously, the auto-cleaning and auto-zeroing system for use with a PID has a by-pass conduit which takes ambient air from the 4/2 valve after passing through the $2^{nd}$ conduit, so that ambient air by pass the ionization chamber.

Preferably, the auto-cleaning and auto-zeroing system for use with a PID, has a continuous motor to continuously operate a pump to draw cyclically ambient gas from a source of ambient gas for measurement of ambient gas during a measurement cycle and then draw ambient air from the environment, said auto-cleaning and auto-zeroing system when drawing ambient air from the environment, operating in these cycles:
 a measurement cycle; followed by
 a cleaning (flushing) cycle; followed by
 a cleaning (ionization) cycle
wherein the cycle starts again.

Preferably, during the cleaning (flushing) cycle of an auto-cleaning and auto-zeroing system for use with a PID, the system draws ambient air from the surrounding:

said ambient air passes through a cleaning chamber to remove impurities from the ambient air; so that only cleaned and filtered air flows out from the cleaning chamber into the $2^{nd}$ conduit;

said 4/2 valve operates to direct the cleaned and filtered ambient air into the inlet conduit to enter the ionization chamber;

characterized in that the cleaned and filtered ambient air in the ionization chamber flushes out air borne contaminants and pollutants in the ionization chamber originating from the ionization of ambient gas during the measurement cycle.

Preferably, during the cleaning (ionization) cycle of an auto-cleaning and auto-zeroing system for use with a PID, the system draws ambient air through the $2^{nd}$ conduit;

said ambient air passes through a cleaning chamber to remove impurities from the ambient air; so that only cleaned and filtered air flows out from the cleaning chamber into the $2^{nd}$ conduit;

said 4/2 valve operates to direct the cleaned and filtered ambient air into the by-pass conduit, by-passing the ionization chamber;

the splitter connector allows ambient air from the cleaning (flushing) cycle left inside the ionization chamber; to be trapped within the ionization chamber, thereby allowing the cleaned and filtered ambient air to be ionized and the air borne contaminants and pollutants deposited in the ionization chamber to be removed.

Preferably, during the cleaning (flushing) cycle of an auto-cleaning and auto-zeroing system for use with a PID, the splitter connector allows air borne contaminants and pollutants flushed out from the ionization chamber during the cleaning (flushing) cycle to pass through the outflow conduit into the environment.

Preferably, during the cleaning (ionization) cycle of an auto-cleaning and auto-zeroing system for use with a PID, the splitter connector allows ambient air from the cleaning (flushing) cycle left inside the ionization chamber to be trapped within the ionization chamber, thereby allowing the cleaned and filtered ambient air to be ionized and the air borne contaminants and pollutants deposited in the ionization chamber to be removed.

Preferably, the auto-zeroing function is carried out by passing ambient air through the cleaning chamber to remove all air borne impurities, and then through the $2^{nd}$ conduit into the inlet conduit via the 4/2 valve, and entering the ionization chamber for the taking of a measurement of the cleaned and filtered ambient air.

A second object of the Invention is an auto-cleaning and auto-zeroing system, said system comprising:

more than one $1^{st}$ conduit for flow of ambient gas;
more than one $2^{nd}$ conduit for flow of ambient air;
each of the $2^{nd}$ conduit having a chamber to remove impurities from ambient air; and
more than one 4/2 valve;
more than one splitter connector
more than one continuous motor; and
more than one continuous operating pump A third object of the invention is an auto-cleaning and auto-zeroing system for use with a PID, the PID having a $1^{st}$ conduit for inflow of ambient gas to be measured in the ionization chamber of the PID, during a measurement cycle, the system having:

a continuous motor to continuously operate a pump to draw ambient gas from a source of ambient gas or ambient air from the environment,
a $2^{nd}$ conduit for flow of ambient air;
a cleaning chamber which removes pollutants and contaminants in the ambient air;
a three way valve to continuously direct a cyclical flow of ambient gas followed by a flow of ambient air into the ionization chamber;

characterized in that the cleaned ambient air in the $2^{nd}$ conduit is drawn by the continuous motor, via the three way valve, into the ionization chamber to flush out air borne contaminants and pollutants in the ionization chamber originating from the ionization of ambient gas during the measurement cycle.

Preferably, the auto-cleaning and auto-zeroing system for use with a PID has a continuous motor to continuously operate a pump to draw ambient gas from a source of ambient gas for the measurement of the ambient gas during a measurement cycle and to draw ambient air from the environment to flush the air borne contaminants and pollutants in the ionization chamber during a cleaning cycle.

Preferably, during the cleaning cycle of an auto-cleaning and auto-zeroing system for use with a PID, the system draws ambient air through the $2^{nd}$ conduit;

said ambient air passes through a cleaning chamber to remove impurities from the ambient air so that only cleaned and filtered air flows out from the cleaning chamber; and 3 way valve operates to allow flow of cleaned and filtered ambient air from the cleaning chamber in the $2^{nd}$ conduit to pass into the ionization chamber;

characterized in that cleaned and filtered ambient air in the ionization chamber flushes out and removes the ionized air borne contaminants and pollutants deposited in the ionization chamber.

Preferably, the auto-zeroing function of the auto-cleaning and auto-zeroing system is carried out by passing ambient air through the cleaning chamber to remove all air borne impurities, and then into the ionization chamber for the taking of a measurement of the cleaned and filtered ambient air.

Preferably, the cleaning chamber for a $2^{nd}$ conduit in an auto-cleaning and auto-zeroing system is a scrubbing chamber, which scrubs the ambient air clean from air borne contaminants and pollutants.

Alternatively, the cleaning chamber for a $2^{nd}$ conduit in an auto-cleaning and auto-zeroing system is a filtering chamber, which filters and remove air borne contaminants and pollutants from the ambient air.

Alternatively, the cleaning chamber for a $2^{nd}$ conduit in an auto-cleaning and auto-zeroing system is an air purification chamber, which purify the ambient air.

Preferably, the cleaning chamber of the auto-cleaning and auto-zeroing system contains a mixture of silica, activated carbon and anhydrous calcium sulphate to remove impurities in the ambient air before the ambient air flows into the ionization chamber.

More advantageously, the filtering chamber of the auto-cleaning and auto-zeroing system contains a plurality of filters to remove impurities in the ambient air before the ambient air flows into the ionization chamber.

More advantageously, the air purification chamber of the auto-cleaning and auto-zeroing system is a combination of a plurality of filters and chemicals to remove impurities in the ambient air before the ambient air flows into the ionization chamber.

More advantageously the auto-cleaning and auto-zeroing system has one or more continuous motors.

More advantageously, the auto-cleaning and auto-zeroing system has one or more continuous pumps.

More advantageously the auto-cleaning and auto-zeroing system has one motor for each pair of $1^{st}$ conduit and each $2^{nd}$ conduit.

More advantageously, the cleaning chamber for an auto-cleaning and auto-zeroing system has a sensor to indicate the level of chemicals used up in absorbing the impurities so that the chemicals in the scrubbing chamber can be changed.

More advantageously the filtering chamber for an auto-cleaning and auto-zeroing system has a sensor to indicate the amount of impurities trapped by the filters so that the filters in the filtering chamber can be changed.

More advantageously the air purification chamber for an auto-cleaning and auto-zeroing system has a sensor to indicate the amount of impurities trapped in the air purification chamber so that the filters and chemicals in the air purification chamber can be changed Preferably the auto-cleaning and auto-zeroing system has a microprocessor to control the operation of the valves.

Preferably, the auto-cleaning and auto-zeroing system has a microprocessor to monitor the sensor in the cleaning chamber.

More advantageously, the auto-cleaning and auto-zeroing system has a microprocessor to perform the auto-zeroing measurement.

Preferably, the auto-cleaning and auto-zeroing system has a microprocessor to monitor and operate the auto-cleaning and auto-zeroing system.

BRIEF DESCRIPTION OF THE DRAWINGS

For a better understanding of the invention, its advantages, and the objects attained by its use, reference should now be made to the accompanying drawings. The accompanying drawings illustrate one or more embodiments of the invention and together with the description herein, serve to explain the workings and principles of the invention.

DETAILED DESCRIPTION OF THE PREFERRED EMBODIMENT

Figure 1:
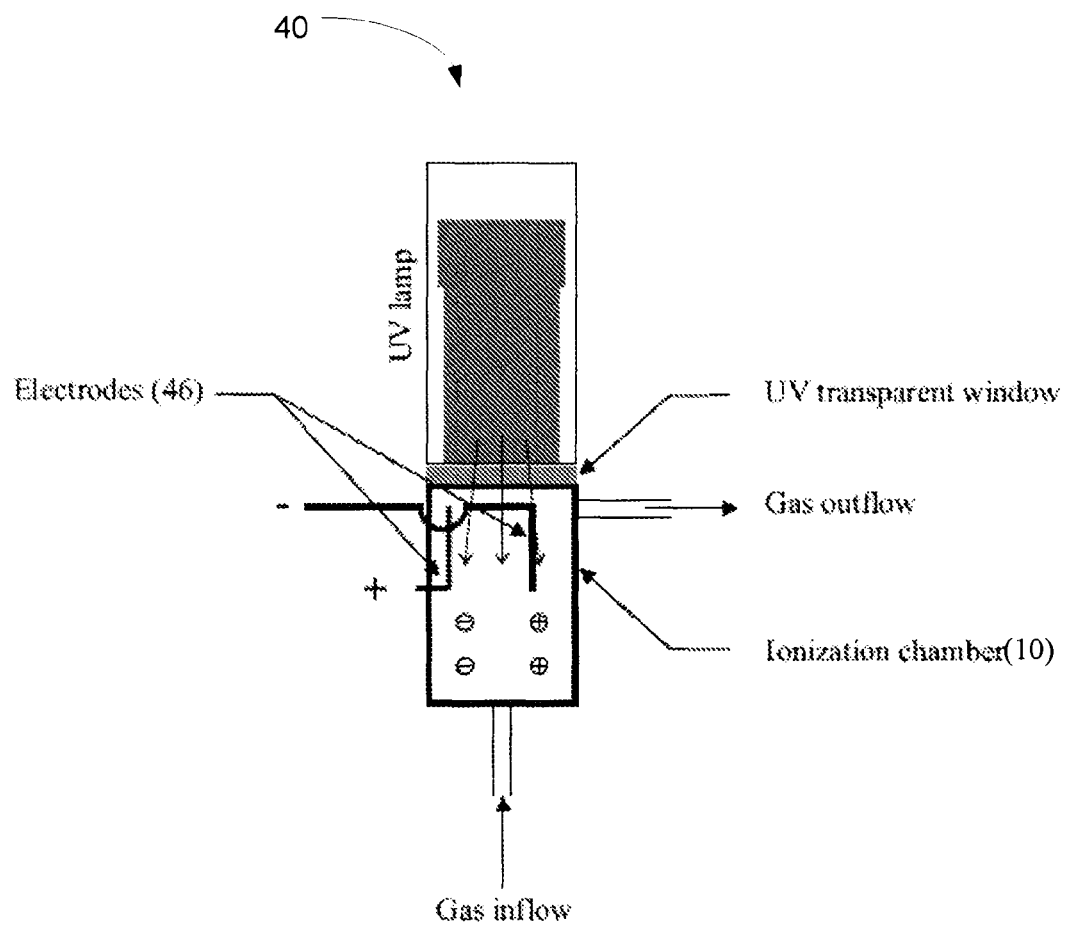
FIG. 1 is an illustration of a simple PID device known in the art.

FIG. 1 is an illustration of a simple PID device (40) known in the art. The PID device (40) has an UV lamp through which UV light is shone through an optically clear window into an ionization chamber (10).

The novel features of the auto-cleaning and auto-zeroing system (1) of this invention is a 4/2 valve (30) and the use of two conduits (20,22) to control and regulate alternatively, the flow of ambient gas (16) and clean filtered air into the ionization chamber (10). The ambient gas (16) flows through a $1^{st}$ conduit (20) into the ionization chamber (10) without passing through any cleaning chamber (12) to remove pollutants and contaminants in the ambient gas (16). Ambient air (18) flows through a $2^{nd}$ conduit (22) through a cleaning chamber (12) which removes air borne dust particles, pollutants and gaseous materials. Ambient air (18) is thus cleaned and filtered before being entering the ionization chamber (10).

Figure 2:
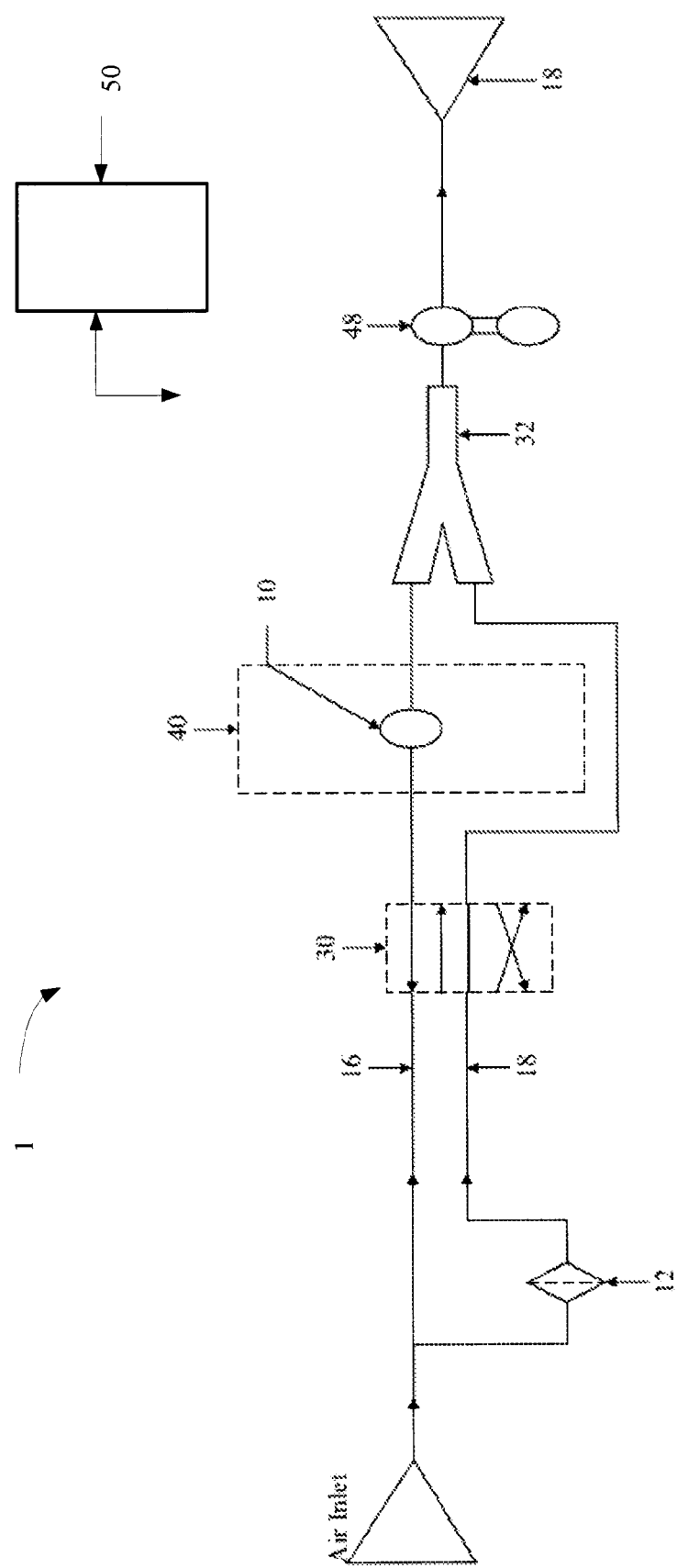
FIG. 2 shows the auto-cleaning and auto-zeroing system used on the PID device.

FIG. 2 shows the auto-cleaning and auto-zeroing system (1) of the invention used with a PID device (40).

The flow of gas through the auto-cleaning and auto-zeroing system (1) is from left to right. The auto-cleaning and auto-zeroing system (1) comprises of a continuous operation pump (48), wherein the pump (48) brings in ambient gas (16) (into a $1^{st}$ conduit (20), and ambient air (18) into a $2^{nd}$ conduit (22). A 4/2 valve (30) operates to allow ambient gas (16) to flow through the $1^{st}$ conduit (20). The 4/2 valve (30) also operates to allow ambient air (18) to flow through the $2^{nd}$ conduit (22) to go into the ionization chamber (10) or to by-pass the ionization chamber (10). The ambient air (18) passes through a cleaning chamber (12) to remove air borne pollutants and gaseous materials so that only cleaned and filtered ambient air (18) enter the ionization chamber (10). Both the ambient gas (16) and cleaned and filter ambient air (18) flows into the ionization chamber (10) through an inlet conduit (24) via the 4/2 valve (30) which operates alternatively to allow passage of ambient gas (16) [from the $1^{st}$ conduit (20)] into the ionization chamber (10) of the PID (40) for measurement or passage of cleaned and filtered ambient air (18) [from the $2^{nd}$ conduit (22)] into the ionization chamber (10) of the PID device (40) to flush the contaminants and pollutants which have settled on the electrodes (46), the ionization chamber (10), the PID (40) window. Both the ambient gas (16) and ambient air (18) passes out from the ionization chamber (10) through an outflow conduit (28) and eventually through an air outlet into the atmosphere. The ambient air (18) will carry in it the contaminants and pollutants from the ionization chamber (10), having flushed these out into the atmosphere via the air outlet.

Ambient air (18) is also passed directly through the $2^{nd}$ conduit (22) through a by-pass conduit (29) during an ionization phase (10) in the cleaning cycle.

The principle of this invention is the operation of an continuous cycle of measurement, cleaning (flushing) and cleaning (ionization). During the measurement cycle, ambient gas (16) will leave behind contaminants and pollutant in the ionization chamber (10). During the cleaning (flushing) cycle, cleaned and filtered ambient air (18) is passed through the $2^{nd}$ conduit (22) and inlet conduit (24) into the ionization chamber (10) to flush out the contaminants and pollutants which have settled on the electrodes (46), the ionization chamber (10), the PID (40) window. After the ambient air (18) had carried away the pollutants and contaminants from the ionization chamber (10) during the cleaning (flushing) cycle, ambient air (18) in the $2^{nd}$ conduit (22) is now directed by the 4/2 valve (30) into the by-pass conduit (29). As the cleaned and filtered ambient air (18) by-pass the ionization chamber (10), the cleaned and filtered air (18) remaining in the ionization chamber (10) will ionize the remaining pollutants contaminants left on the surfaces of the ionization chamber (10).

Through this continuous cycle of passing ambient gas (16) (measurement cycle), passing clean and filtered ambient air (18) into the ionization chamber (10) (cleaning flushing cycle) to flush out contaminants and pollutants in ionization chamber (10), followed by an ionization cycle wherein pollutants and contaminants are ionized (cleaning ionization cycle), the pollutants and contaminants are not given any opportunity to settle onto the electrodes (46) and PID (40) window. As such, layers of pollutants and contaminants will not be allowed to be deposited over the electrodes (46), walls and PID (40) window within the ionization chamber (10). Any newly deposited layer of pollutants and contaminants formed on the electrodes (46), walls and window of the ionization chamber (10) can thus be easily removed. In this manner, the gas measurement sensor in the PID (40) device is always ready to give accurate measurements. Since the pollutants and contaminants are always flushed out of the ionization chamber (10) with the inflow of cleaned and filtered ambient air (18), the ionization chamber (10) is always kept quite free of pollutants and contaminants, thereby reducing the necessity to stop the operation of the PID (40) device for maintenance, in order to clean the PID (40) window and electrodes (46).

The operation of the auto-cleaning and auto-zeroing system (1) will be illustrated by reference to FIG. 3, 4 and FIG. 5.

Figure 3:
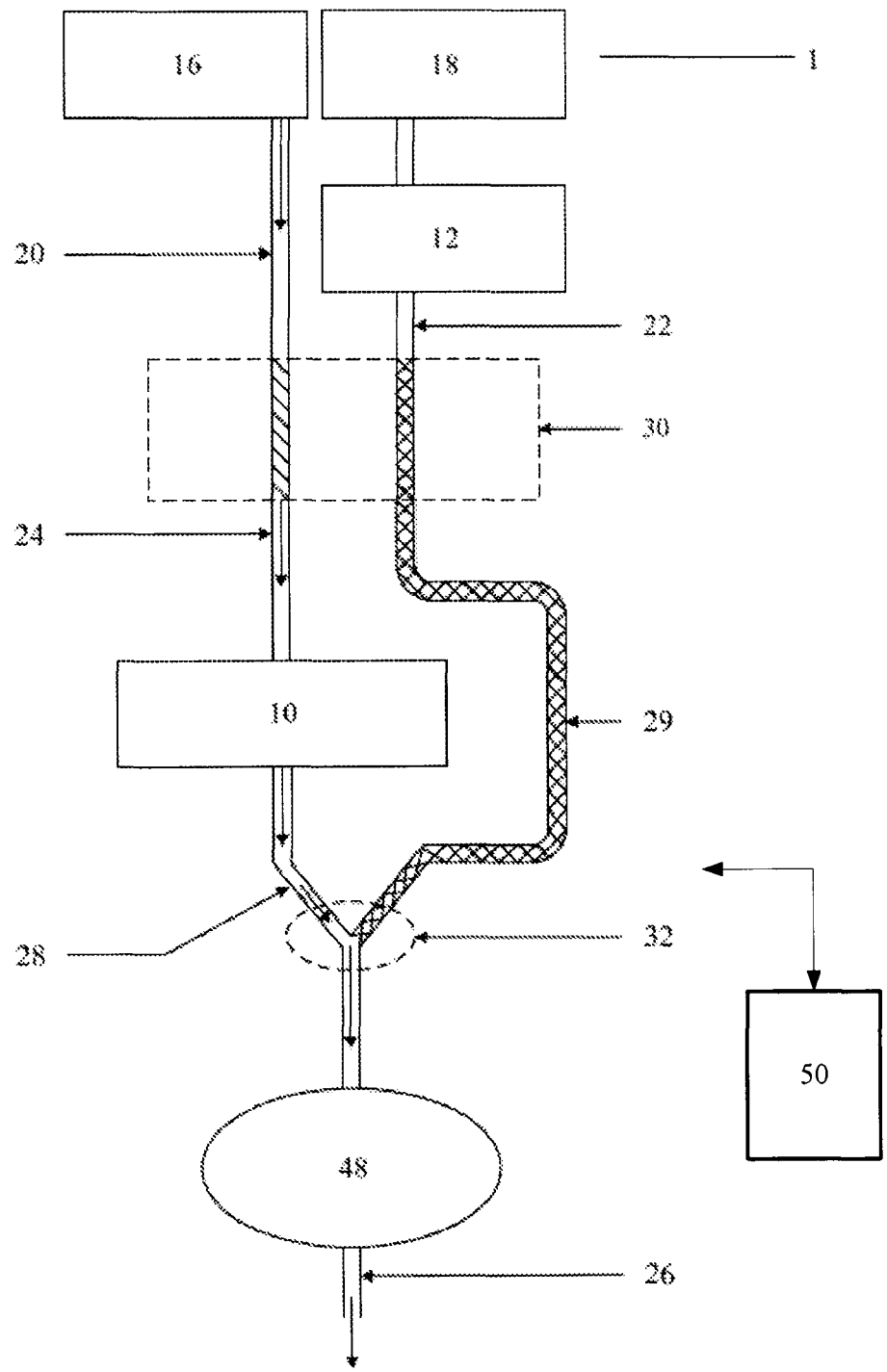
FIG. 3 shows the flow of ambient gas during the measurement cycle in the operation of the auto-cleaning and auto-zeroing system.

FIG. 3 shows the flow of ambient gas (16) during the measuring cycle in the operation of the PID (40) device.

In the measurement cycle, the continuous operation pump (48) will bring in ambient gas (16) through the $1^{st}$ conduit (20), through the 4/2 valve (30). The ambient gas (16) passes through the inlet conduit (24) and straight into the ionization chamber (10) wherein the gas measurement process takes place. The ambient gas (16) does not pass through any cleaning chamber (12) since the 4/2 valve (30) is turned on to bring the ambient gas (16) through the $1^{st}$ conduit (20) and inlet conduit (24). As such, the ambient gas (16) could be measured accurately during the measurement cycle.

Figure 4:
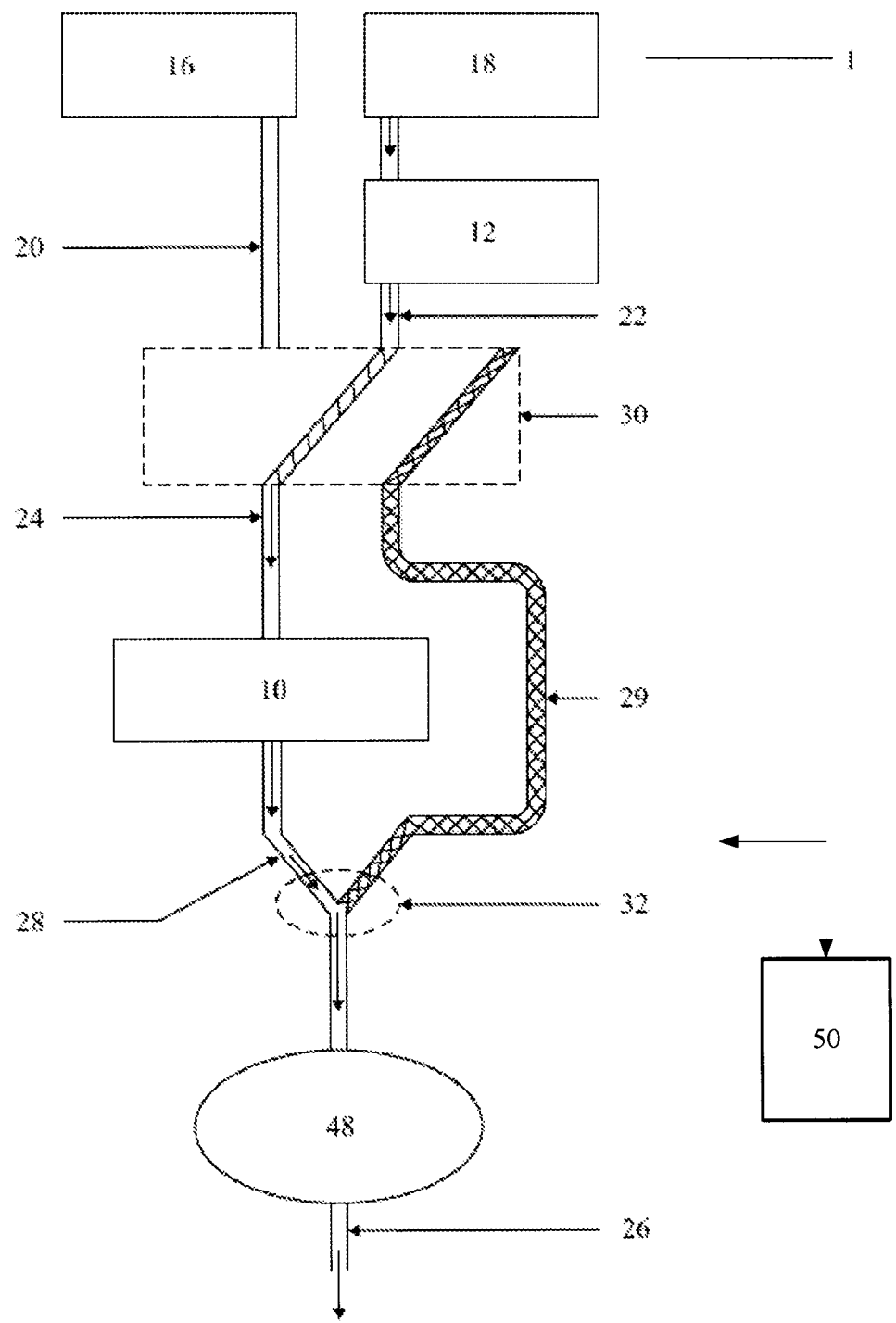
FIG. 4 shows the flow of ambient air during the cleaning (flushing) cycle in the operation of the auto-cleaning and auto-zeroing system.

FIG. 4 shows the flow of ambient air (18) during the cleaning (flushing) cycle in the operation of the auto-cleaning and auto-zeroing system (1).

After the measurement cycle, the 4/2 valve (30) is switched to connect the $2^{nd}$ conduit (22) for ambient air (18) intake. The continuous operation pump (48) now brings in ambient air (18) through a cleaning chamber (12), which removes all air borne contaminants and gaseous materials in the ambient air (18). The cleaned and filtered ambient air (18) in the $2^{nd}$ conduit (22) then passes through the inlet conduit (24) and into the ionization chamber (10), to flush out any recently formed pollutants and contaminants which have settled on the electrodes (46), the PID (40) window and the ionization chamber (10) itself. As these pollutants and contaminants are recently formed, these can be easily removed and carried out by the jet of cleaned and filtered ambient air (18) rushing into the ionization chamber (10), and out of the ionization chamber (10), through the outflow conduit (26), through a splitter connector (32) and eventually into the open. In this manner, the pollutants and contaminants are flushed out into the environment.

Figure 5:
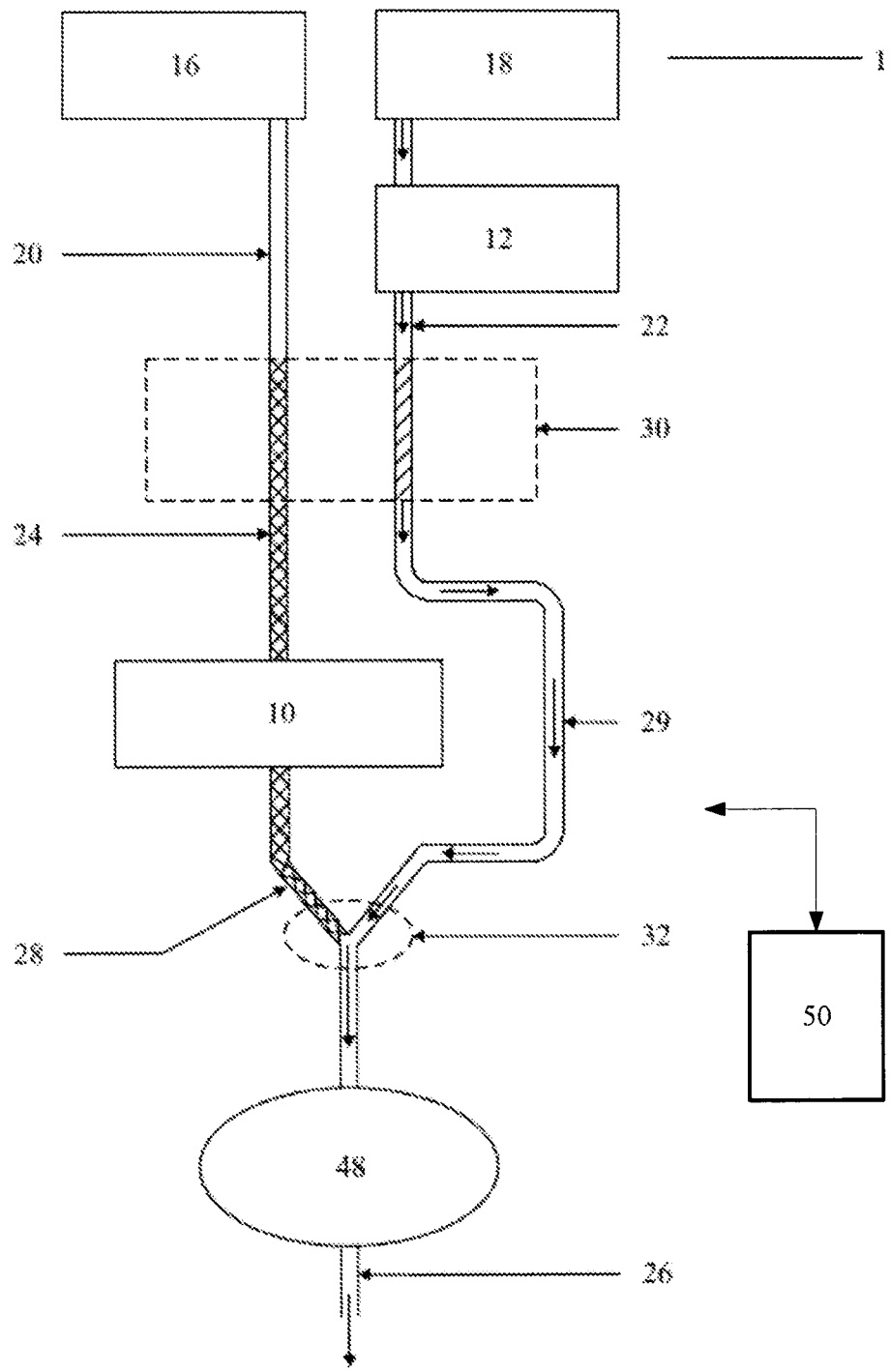
FIG. 5 shows the flow of ambient air during the cleaning (ionization) cycle in the operation of the auto-cleaning and auto-zeroing system.

FIG. 5 shows the flow of ambient air (18) during the cleaning (ionization) cycle in the operation of the auto-cleaning and auto-zeroing system (1).

After the cleaning (flushing) cycle, the auto-cleaning and auto-zeroing system (1) moves to the cleaning (ionization) cycle. The 4/2 valve (30) is now switched to connect the $2^{nd}$ conduit (22) to the by-pass conduit (29). The continuous operation pump now brings in ambient air (18) through the $2^{nd}$ conduit (22) and into the by-pass conduit (29). When ambient air (18) is passing through the by-pass conduit (29), the splitter connector (32) allows ambient air (18) from the cleaning (flushing) cycle left inside the ionization chamber (10), to be trapped. In the meantime, the ambient air (18) trapped within the ionization chamber (10), from the cleaning (flushing) cycle, is further ionized. The removal of the recently formed pollutants and contaminants takes advantage of the fact that ozone may be formed from $O_2$ by electrical discharges and by action of high energy electromagnetic radiation. It is known that certain electrical equipment generate significant levels of ozone and this is true of devices using high voltages, such as ionic air purifiers, laser printers, photocopiers. Thus $O_2$, present in the cleaned and filtered ambient air (18) remaining in the ionization chamber (10) will undergo ionization too in the ionization chamber (10) of the PID (40). The ozone formed in the ionization chamber (10) ionize and remove the recently deposited small quantities of pollutants and contaminants left after the measurement cycle.

It can be seen from the workings of continuous operation pump (48) and the 4/2 valve (30), the measurement, cleaning (flushing) and cleaning (ionization) cycles moves from each cycle continuously. In this manner, the accuracy of gas measurement function of the PID (40) device can be assured since all air borne pollutants and contaminants are continuously removed by cleaning (through flushing of air borne contaminants and pollutants) and by cleaning (through ionization of the pollutants and contaminants) of the electrodes (46), the PID (40) window and the ionization chamber (10). The inventive auto cleaning and auto-zeroing system (1) thereby will almost reduce the necessity for stopping the operation of the PID (40) device for cleaning and maintenance. In addition, the inventive system has auto-zeroing capability too. The system is capable of using the zero-gas state of the cleaned and filtered ambient air (18) to carry out auto-zeroing at every run-time cycle. Therefore the inventive auto-cleaning and auto-zeroing system (1) used with a PID (40) comprises a continuous operation pump (48), a 1st conduit (20) for ambient gas (16), a $2^{nd}$ conduit (22) for ambient air (18), a cleaning chamber (12) in the $2^{nd}$ conduit (22) for removal of air borne contaminants and gaseous materials so that clean and filtered ambient air (18) enters the ionization chamber (10), and a 4/2 valve (30) for flow of either ambient gas (16) or ambient air (18) into the ionization chamber (10) and for flow of ambient air (18) to by-pass the ionization chamber (10), via a splitter connector (32) moving continuously from a measurement cycle to a cleaning (flushing) cycle and to a cleaning (ionization) cycle.

DETAILED DESCRIPTION OF WORKING OF PREFERRED EMBODIMENT

In operation, the PID (40) device operates continuously to measure the flow of ambient gas (16). As described earlier, the continuous operation of the PID (40) device will cause air borne contaminants and pollutants to be deposited onto the electrodes (46), the PID (40) window and even the walls of the ionization chamber (10). The operation of the PID (40) device would have to be stopped for maintenance and the PID (40) cleaned to remove these contaminants and pollutants, and then have to be re-calibrated before being put back into operation.

By introducing an auto-cleaning and auto-zeroing system (1) to bring both ambient gas (16) and cleaned and filtered ambient air (18) into the PID (40) device, the necessity for maintenance and cleaning of the PID (40) device can be substantially eliminated. The auto-cleaning and auto-zeroing system (1) comprises:
- a $1^{st}$ conduit (20) for ambient gas (16) to be measured which leads to a 4/2 valve (30) and an inlet conduit (24) before going into the ionization chamber (10) of the PID (40) device;
- a $2^{nd}$ conduit (22) for ambient air (18) which leads from a cleaning chamber (12) through the 4/2 valve (30), through an inlet conduit (24) and into the ionization chamber (10) of the PID (40) device;
- a cleaning chamber (12) to remove dust particles, other air borne pollutants and other gaseous materials from ambient air (18), thus allowing cleaned and filtered ambient air (18) to enter the $2^{nd}$ conduit (22) before going into the ionization chamber (10) of the PID (40) device;
- a 4/2 valve (30) which allows ambient gas (16) [through the $1^{st}$ conduit (20)] or cleaned and filtered ambient air (18) [through the $2^{nd}$ conduit (22)] to enter the ionization chamber (10) of the PID (40) device or cleaned and filtered ambient air (18) [through the $2^{nd}$ conduit (22) and then through the by-pass conduit (29)] to by-pass the ionization chamber (10); and
- a splitter connector (32) leading from either an outflow conduit (28) from the ionization chamber (10) or from the by-pass conduit (29), to a continuous pump (48) and then leading to an air outlet conduit (26). The splitter connector (32) allows outflow of ambient gas (16) or ambient air (18) from the ionization chamber (10) or outflow of ambient air (18) passing though the $2^{nd}$ conduit (22) and by-pass conduit (29).
- a continuous operation pump (48) to draw ambient air (18) or ambient gas (16) to be measured through the auto-cleaning and auto-zeroing system (1) into the ionization chamber (10) before removing the ambient air (18) or ambient gas (16) from the ionization chamber (10) and also draw ambient air (18), through the $2^{nd}$ conduit (22) and by-pass conduit (29), to by-pass the ionization chamber (10).
- an outflow conduit (26) for passage of the ambient gas (16) and ambient air (18) carrying air borne pollutants and contaminants from the cleaning (flushing cycle) or ambient air (18) carrying ionized particles from the cleaning (ionization cycle) through an outlet conduit (26), into the atmosphere The continuous pump (48) is placed after the ionization chamber (10), thus effectively drawing ambient gas (16) or ambient air (18) through the auto-cleaning and auto-zeroing system (1) and into the ionization chamber (10). The location of the continuous pump (48) after the ionization chamber (10) is to avoid gas memory effects on the inner pump materials. Ambient gas (16) is thus drawn into a $1^{st}$ conduit (20), and ambient air (18) is drawn into a $2^{nd}$ conduit (22). Ambient air (18) is brought through a cleaning chamber (12) to remove air borne dust particles, pollutants and other gaseous materials before passing through the $2^{nd}$ conduit (22) so that the ambient air (18) is filtered and cleaned before entering the ionization chamber (10) via the 4/2 valve (30).

The cleaning chamber (12) acts as to "scrub" the ambient air (18) to remove air borne dust particles, pollutants and other gaseous materials in the ambient air (18) so that only clean and filtered air enters the ionization chamber (10).

The cleaning chamber (12) can be a filtering chamber to remove air borne dust particles, pollutants and other gaseous materials in the ambient air (18) so that only clean and filtered air enters the ionization chamber (10).

The cleaning chamber (12) can be an air purification chamber which uses a combination of filters and chemicals to remove air borne dust particles, pollutants and other gaseous materials in the ambient air (18) so that only clean and filtered ambient air (18) enters the ionization chamber (10).

The scrubbing agent used in the cleaning chamber (12) depends on the composition of ambient air (18) in the place of operation of the PID (40) device. The scrubbing agent could contain chemicals in liquid form or solid form or could be a combination of both. The chemicals typically used are a mixture of silica, activated carbon and anhydrous calcium sulphate.

The filtering chamber may have a plurality of various types of filters, to remove the tiny pollutants and contaminants in the ambient air (18).

The air purification chamber is a combination of filters and chemicals, to remove air borne dust particles, pollutants and other gaseous materials in the ambient air (18) so that only clean and filtered ambient air (18) enters the ionization chamber (10).

The 4/2 valve (30) operates continuously and to allow:
- passage of ambient gas (16) into the ionization chamber (10) of the PID (40) for measurement of ambient gas (16), referred to as "measurement cycle"; then
- passage of cleaned and filtered ambient air (18) into the ionization chamber (10) of the PID (40) to flush out the air borne contaminants and pollutants which have been formed within the ionization chamber (10), referred to as "cleaning (flushing) cycle"; and then
- passage of cleaned and filtered ambient air (18) to by-pass the ionization chamber (10), allowing oxygen in the ambient air (18) remaining in the ionization chamber (10) (from the cleaning [flushing] cycle) to be converted to ozone to remove the newly formed pollutants and contaminants on the electrodes, the ionization chamber (10), the PID (40) window, thereby removing these pollutants and contaminants from the electrodes, walls of ionization chamber (10) and PID (40) window. This is referred to as "cleaning (ionization) cycle".

It can be seen that the continuous operation pump (48) works through these cycles:
- a measurement cycle in which ambient gas (16) goes into the ionization chamber (10) and is measured; followed by
- a cleaning (flushing) cycle in which filtered and cleaned ambient air (18) goes into the ionization chamber (10) to flush out air borne contaminants and pollutants in the ionization chamber (10); followed by
- a cleaning (ionization) cycle in which filtered and cleaned ambient air (18) by-passes the ionization chamber (10), allowing the oxygen in the ambient air (18) remaining in the ionization chamber (10) to oxidize the newly formed contaminants and pollutants left on the electrodes (46), walls of the ionization chamber (10) and PID (40) window, thus cleaning the interior of the PID (40), particularly the electrodes (46) and PID (40) window.

In operation, a microprocessor (50) controls the operation of the continuous pump (48), the operation of auto-cleaning function of the inventive system through operations of the 4/2 valve (30) through the measurement cycle, cleaning (flushing) cycle and cleaning (ionization) cycle as well as the auto-zeroing function of the inventive system of the PID (40) device. The microprocessor (50) also has the electrical circuits for operating the following:
- a lamp driver circuit that drives the UV lamp;
- a bias driver circuit that drives the bias electrode (46);
- a sense driver circuit that drives the sense electrode (46);
- a pump driver circuit that drives the continuous operation pump (48);
- a valve circuit that drives the 4/2 valve (30);
- a cleaning chamber (12) driver circuit which drives the cleaning chamber (12) which may be a scrubbing chamber or a filtering chamber or an air purification chamber; and
- an auto-zeroing measurement circuit which carries out the auto-zeroing function The microprocessor (50) may also have sensor circuits to detect usage of chemicals and level of contamination in the chemicals and filters used in the various types of chamber proposed in the inventive system.

When the PID (40) device is in operation, the auto-cleaning and auto-zeroing system (1) of the invention would be operating continuously from the measurement cycle to the cleaning (flushing) cycle and then to the cleaning (ionization) cycle. The processes which take place inside the ionization chamber (10) during the measurement cycle and cleaning cycles are described below.

Measurement Cycle

The continuous operating pump (48) firstly draws in ambient gas (16) from a source of gas or ambient air (18) from the surrounding. The 4/2 way valve (30) then switches to allow ambient gas (16) in the $1^{st}$ conduit (20) to be drawn through the inlet conduit (24) into the ionization chamber (10) of the PID (40). When the ambient gas (16) is in the ionization chamber (10), measurement of the ambient gas (16) is carried out through the ionization process. As the ambient gas (16) is passed through the window of PID (40) where the UV lamp is situated, the ambient gas (16) molecules are heated, emitting light particles, or photons of high UV energy. Thus photo-ionization of the gas molecules occurs when a photon is adsorbed by the molecule, generating two electrically charged fragments, or ions, one positively charged, X+, and one negatively charged, Y−. As a result of this ionization process, the gas molecules are no longer neutral and begin to drift to the negative electrode of the applied electrical field. Once arrived on the negatively charged sense electrode, the gas ions capture an electron form the electrode (46) and produce a current which is being measured. The produced free electrons drift in the opposite direction and are captured by the bias electrode. The ions and electrons drift form a closed circuit where the measurement current begins to flow. With a continuous photon flow and constant gas flow, the measured current is directly proportional to the gas concentration.

It is during this ionization process that pollutants such as dirt particles, oil particles, fluxes, water particles and other contaminants are deposited on the electrodes (46), the PID (40) window and the ionization chamber (10). After the ambient gas (16) is passed through the ionization chamber (10), it is drawn out by the continuous operating pump (48), leaving behind the pollutants and contaminants which have settled on the electrodes (46), inner walls of the ionization chamber (10) and PID (40) window.

Cleaning (Flushing) Cycle

At the commencement of the cleaning (flushing) cycle, the microprocessor (50) switches the 4/2 valve (30) to allow ambient air (18) to be drawn from the surrounding. The ambient air (18) is then forced through a cleaning chamber (12). The cleaning chamber (12) can be a scrubbing chamber or a filtering chamber or an air purification chamber. The cleaning chamber (12) removes the air borne contaminants, pollutants and other gaseous materials in the ambient air (18). After passing through the cleaning chamber (12), the ambient air (18) is now cleaned and filtered. The cleaned and filtered ambient air (18) is then drawn through the 2nd conduit (22), via the 4/2 valve (30), into an inlet conduit (24) and then into the ionization chamber (10) of the PID (40). Once inside the ionization chamber (10), the cleaned and filtered ambient air (18) will flush out air borne pollutants and contaminants left in the ionization chamber (10) by the ambient gas (16) after the measurement cycle.

Immediately the ambient air (18) is drawn out by the continuous operating pump (48), carrying out the air borne pollutants and contaminants before these pollutants and contaminants to settle on the electrodes (46), inner walls of the ionization chamber (10) and PID (40) window. The splitter connector (32) is switched to allow passage of the ambient air (18) with its air borne pollutants and contaminants to be drawn through the outflow conduit (28) and through the outlet conduit (26), into the atmosphere Cleaning (Ionization) Cycle After the cleaning (flushing) cycle, the microprocessor switches the 4/2 valve (30) to allow ambient air (18) to be drawn in to start the cleaning (ionization) cycle. Ambient air (18) is forced through a cleaning chamber (12). After passing through the cleaning chamber (12), the ambient air (18) now passes through the $2^{nd}$ conduit (22) and then through the by-pass conduit (29) without going through the ionization chamber (10) of the PID (40). At the same time, inside the ionization chamber (10), there is still cleaned and filtered ambient air (18) left inside the ionization chamber (10). The splitter connector (32) allows, ambient air (18) from the cleaning (flushing) cycle left in the ionization chamber (10) to be trapped. The oxygen in the ambient air (18) will oxidizes the pollutants and contaminants which have settled on the electrodes (46), inner walls of the ionization chamber (10) and PID (40) window. The removal of the recently formed pollutants and contaminants takes advantage of the fact that ozone is formed from $O_2$ by electrical discharges in the ionization chamber (10) of the PID (40). The ozone formed in the ionization chamber (10) ionizes the pollutants and contaminants recently deposited on the electrodes (46), inner walls of the ionization chamber (10) and PID (40) window.

The cleaning chamber (12) may include a sensor to detect the efficacy level of the scrubbing agent and to alert the user should the efficacy level of the scrubbing agent falls below an unacceptable level.

The scrubbing agents used in the cleaning chamber (12) are common chemicals for removing contaminants and pollutants in ambient air (18) and are known in the art, such as mixture of silica, activated carbon and anhydrous calcium sulphate.

The cleaning chamber (12) can consist of a series of filters arranged to remove air borne dust particles, other pollutants and contaminants in ambient air (18).

In place of a cleaning chamber (12), an air purification chamber can also be used. The air purification chamber can be a combination of a number of filters and scrubbing chemicals to remove air borne dust particles, other pollutants and contaminants as well as other types of gases in the environment, which may affect the measurement of ambient gas (16).

Since the PID (40) is self cleaning, there is no necessity to stop its operation for maintenance. Should the PID (40) be slightly dirty, the microprocessor (50) can be programmed to continuously draw in cleaned and filtered ambient air (18) to clear any residue of contaminant and pollutant. Ozone is thus formed from $O_2$ in the ambient air (18) by electrical discharges in the ionization chamber (10) of the PID (40). The ozone formed in the ionization chamber (10) removes the pollutants and contaminants in the ionization chamber (10). Ambient air (18) is cleaned by passing through the cleaning chamber (10) via the $2^{nd}$ conduit (22) and a measurement of the ambient air (18) is taken, for the auto-zeroing exercise. Thus the auto-cleaning and auto-zeroing system (1) for the PID (40) enables the PID (40) to be self cleaning and auto-zeroing.

Auto Zeroing

It is possible that with the continuous cyclical operation of the measurement cycle, cleaning (flushing) cycle and cleaning (ionization) cycle, using the auto-cleaning and auto-zeroing system (1), the ionization chamber (10) may require a zeroing measurement. This is carried out automatically by continuously passing ambient air (18) through the cleaning chamber (12), and passing the cleaned and filtered ambient air (18) into the ionization chamber (10) for a continuous period of cleaning for a period of time before the microprocessor takes a zero-measurement.

After the cleaning of the ionization chamber (10), there may be a requirement to re-zero the PID (40). In using this invention, besides not having to dismantle the PID (40) for cleaning and maintenance, the auto-zeroing function also allows the user to re-zero the PID (40). This is to ensure the gas measurement is accurate. This auto-zeroing measurement carried out by the microprocessor (50).

For re-zeroing, ambient air (18) is passed through the cleaning chamber (12) via the $2^{nd}$ conduit (22) to remove all air borne pollutants and impurities, for a precise measurement. A new zero point measurement is then taken of the cleaned and filtered ambient air (18) in the ionization chamber (10) for the re-zeroing exercise.

With the introduction of an auto-cleaning and auto-zeroing system (1) with the use of a 4/2 valve (30) to bring ambient cleaned and filtered ambient air (18) into the ionization chamber (10) of the PID (40), the PID (40) is thus kept self cleaning. Much time and cost are saved with this inventive auto-cleaning and auto-zeroing system (1).

OTHER EMBODIMENTS

Figure 6:
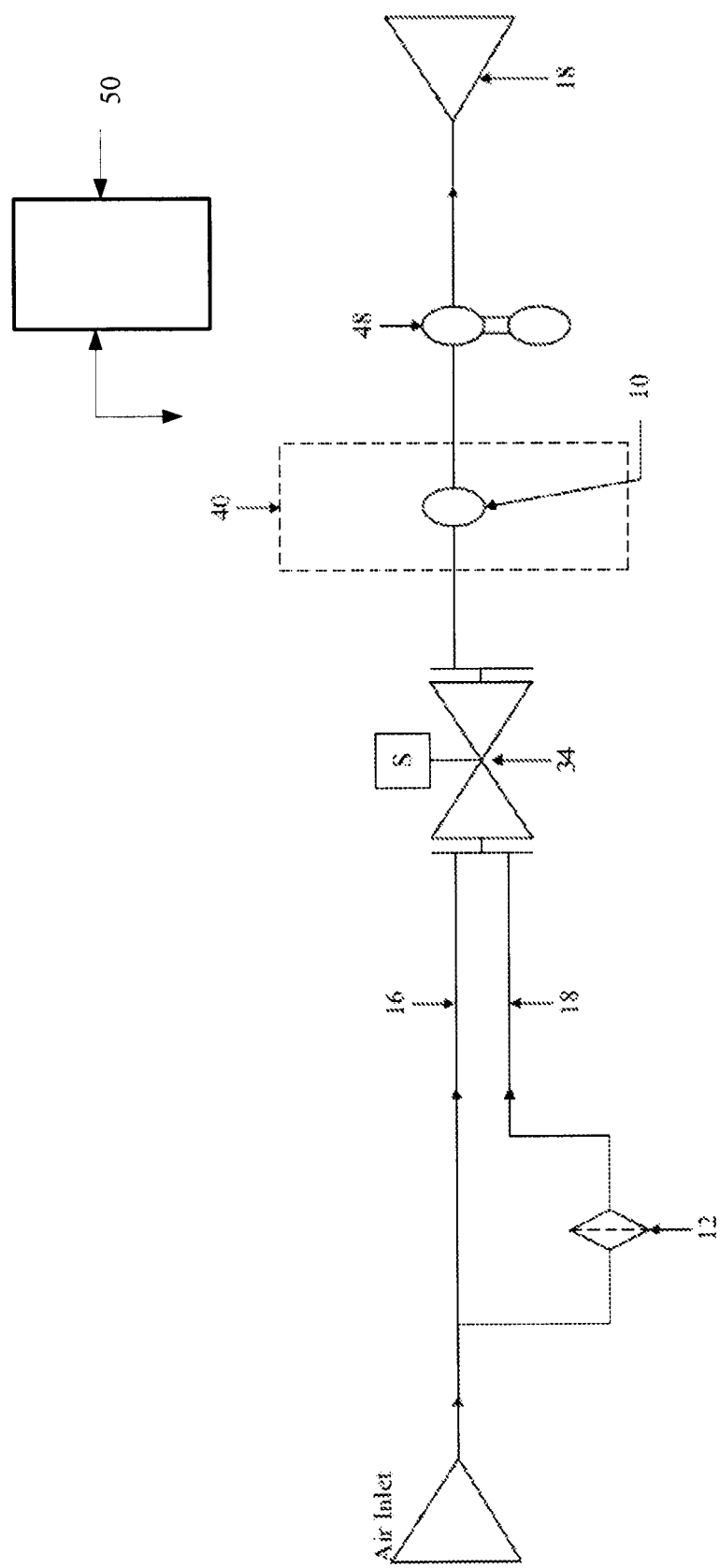
FIG. 6 shows a second embodiment of an auto-cleaning and auto-zeroing system.

FIG. 6 shows a second embodiment of an auto-cleaning and auto-zeroing system (1) without a by-pass conduit (29).

Figure 7:
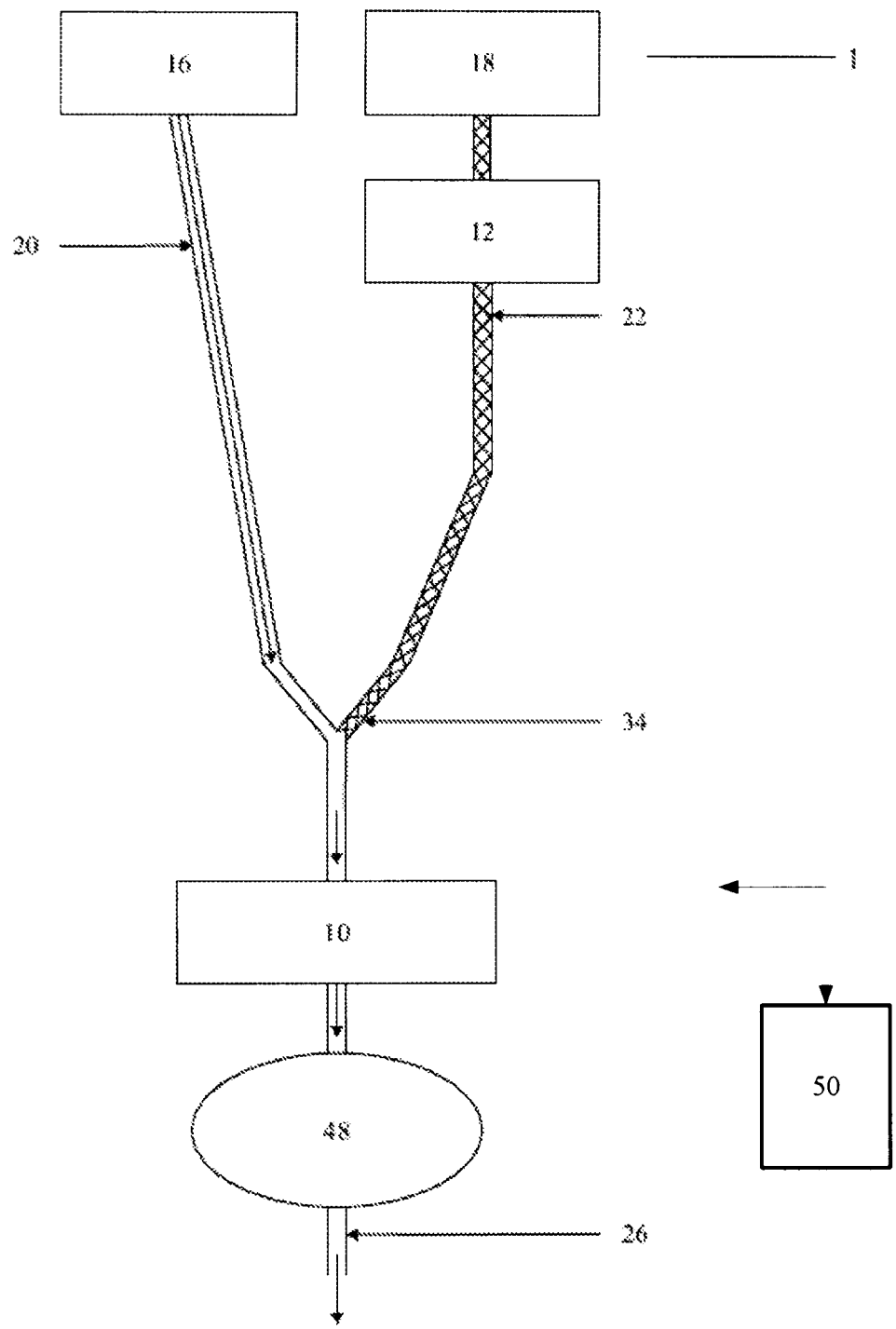
FIG. 7 shows the flow of ambient gas during the measurement cycle in the operation of the second embodiment of the auto-cleaning and auto-zeroing system.

FIG. 7 shows the flow of ambient gas (16) during the measurement cycle in the operation of the second embodiment of the auto-cleaning and auto-zeroing system (1).

Figure 8:
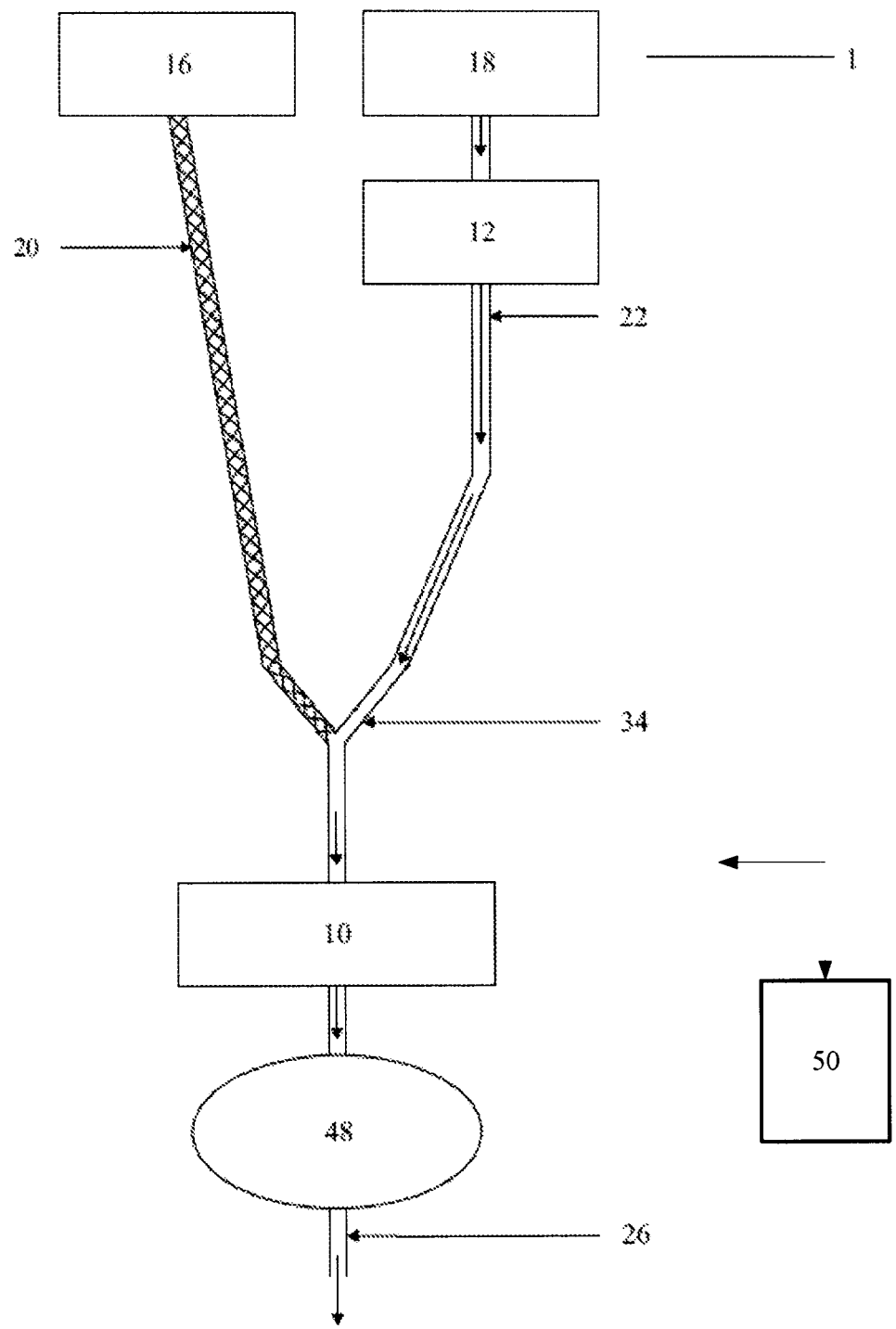
FIG. 8 shows the flow of ambient air during the cleaning cycle in the operation of the second embodiment of the auto-cleaning and auto-zeroing system.

FIG. 8 shows the flow of ambient air (18) during the cleaning cycle in the operation of the second embodiment of the auto-cleaning and auto-zeroing system (1).

In the second embodiment, the valve is a three way valve (34) and not a 4/2 valve (30). Also for the second embodiment, there is no by-pass conduit (29). The configuration for the second embodiment is as follows:
  a $1^{st}$ conduit (20) for ambient gas (16) to be measured which leads to a three way valve (34) before going into the ionization chamber (10) of the PID (40) device;
  a $2^{nd}$ conduit (22) for ambient air (18) which leads to a cleaning chamber (12) before going into a three way valve (34);
  a cleaning chamber (12) to remove dust particles, other air borne pollutants and other gaseous materials thus allowing cleaned and filtered ambient air (18) to enter the three way valve (34) before going into the ionization chamber (10) of the PID (40) device;
  a three way valve (34) which allows passage of ambient gas (16) [in the $1^{st}$ conduit (20)] or cleaned and filtered ambient air (18) [in the $2^{nd}$ conduit (22)] into the ionization chamber (10) of the PID (40) device; and
  a continuous operation pump (48) to cyclically draw ambient air (18) or ambient gas (16) to be measured through the auto-cleaning and auto-zeroing system (1) into the ionization chamber (10) before removing the ambient air (18) or ambient gas (16) from the ionization chamber (10).

The auto-cleaning and auto-zeroing system (1) of the invention as described can have other embodiments. The invention could comprise of a plurality of pairs of $1^{st}$ and $2^{nd}$ conduits (20,22), for example, two or more pairs of $1^{st}$ and $2^{nd}$ conduits (20,22). In such an embodiment, the first pair of conduits comprise of a $1^{st}$ conduit (20) for ambient gas (16) and a $2^{nd}$ conduit (22) for ambient air (18) and the second pair of conduits comprise of a $1^{st}$ conduit (20) for ambient gas (16) and a $2^{nd}$ conduit (22) for ambient air (18).

Another configuration could comprise a plurality of pairs of conduits, but all pairs of conduits could share a common chamber for removal of air borne pollutants and contaminants.

Another configuration could comprise a plurality of pairs of conduits, but all pairs of conduits could share a common continuous operating pump.

Having described preferred embodiments of the invention with reference to the accompanying drawings, it is to be understood that the invention is not limited to the precise embodiment as described herein, and that various changes and modifications may be effected therein by one skilled in the art without departing from the scope or spirit of the invention as defined in the claims.

ADVANTAGEOUS EFFECTS OF THE INVENTION

The invention allows the continuous operation of the PID (40) since it has self cleaning capability and auto-zeroing feature. The auto cleaning and auto-zeroing system (1) therefore eliminates down time caused by regular maintenance of the PID (40) to clean the ionization chamber (10) and to re-zero the PID (40) before re-commencement of use. Maintenance costs are reduced substantially, especially in critical gas measuring applications.

The invention claimed is:

1. An auto-cleaning and auto-zeroing system for use with a Photo-Ionization Detector (PID), said system comprising:
   an ionization chamber having an outflow conduit;
   a first conduit for inflow of ambient gas to be measured;
   a second conduit for flow of cleaned ambient air;
   a cleaning chamber, receiving ambient air from the environment and removing pollutants and contaminants in said ambient air, having an output in communication with said second conduit;
   a valve, in communication with said first conduit and said second conduit, to direct flow from one of said first conduit and said second conduit into said ionization chamber;
   a bypass conduit in communication with an output of said valve;
   a splitter connector having two inlets, a first inlet in communication with the outflow conduit of said ionization chamber and a second inlet in communication with said bypass conduit, and having an outlet, wherein said splitter allows one of said two inlets to pass to said outlet, such that air is trapped in said ionization chamber when said second inlet is in communication with said outlet; and
a continuous motor to continuously operate a pump, the pump disposed downstream from said outlet.

2. The auto-cleaning and auto-zeroing system as claimed in claim 1, wherein said cleaning chamber comprises a scrubbing chamber, which scrubs said ambient air clean from air borne contaminants and pollutants.

3. The auto-cleaning and auto-zeroing system as claimed in claim 2, wherein said cleaning chamber contains a mixture of silica, activated carbon and anhydrous calcium sulphate to remove impurities in said ambient air.

4. The auto-cleaning and auto-zeroing system as claimed in claim 2, wherein said cleaning chamber comprises a sensor to indicate the level of chemicals used up in absorbing impurities so that said chemicals in said scrubbing chamber can be changed.

5. The auto-cleaning and auto-zeroing system as claimed in claim 1, wherein said cleaning chamber comprises a filtering chamber, which filters and removes air borne contaminants and pollutants from said ambient air.

6. The auto-cleaning and auto-zeroing system as claimed in claim 5 wherein said filtering chamber contains a plurality of filters to remove impurities in said ambient air.

7. The auto-cleaning and auto-zeroing system as claimed in claim 5, wherein said filtering chamber comprises a sensor to indicate the amount of impurities trapped by filters so that said filters in said filtering chamber can be changed.

8. The auto-cleaning and auto-zeroing system as claimed in claim 1, wherein said cleaning chamber comprises an air purification chamber, which purifies said ambient air.

9. The auto-cleaning and auto-zeroing system as claimed in claim 8, wherein said air purification chamber comprises a combination of a plurality of filters and chemicals to remove impurities in said ambient air.

10. The auto-cleaning and auto-zeroing system as claimed in claim 9, wherein said air purification chamber comprises a sensor to indicate the amount of impurities trapped in said air purification chamber so that said filters and chemicals in said air purification chamber can be changed.

11. The auto-cleaning and auto-zeroing system as claimed in claim 1, wherein said system comprises more than one continuous motors.

12. The auto-cleaning and auto-zeroing system as claimed in claim 1, wherein said system comprises more than one continuous pumps.

13. The auto-cleaning and auto-zeroing system as claimed in claim 1, wherein said system comprises one motor for each pair of first conduit and second conduit.

14. The auto-cleaning and auto-zeroing system as claimed in claim 1, comprising a microprocessor to control the operation of said valve and said splitter connector.

15. The auto-cleaning and auto-zeroing system as claimed in claim 1, comprising a microprocessor to monitor a sensor in said cleaning chamber.

16. The auto-cleaning and auto-zeroing system as claimed in claim 1, wherein said system has an auto-zeroing mode, wherein said valve, directs flow from said second conduit and said splitter connector directs flow from said outlet conduit, and a measurement is done.

17. The auto-cleaning and auto-zeroing system as claimed in claim 16, comprising a microprocessor to perform said auto-zeroing function.

18. The auto-cleaning and auto-zeroing system as claimed in claim 1, comprising a microprocessor to monitor and operate said auto-cleaning and auto-zeroing system.

19. The auto-cleaning and auto-zeroing system as claimed in claim 1, wherein the system is adapted to operate in a plurality of modes.

20. The auto-cleaning and auto-zeroing system as claimed in claim 19, wherein one of said modes is a measurement cycle, wherein said valve directs flow from said first conduit and said splitter connector directs flow from said outlet conduit.

21. The auto-cleaning and auto-zeroing system as claimed in claim 19, wherein one of said modes is a cleaning (flushing) cycle, wherein said valve directs flow from said second conduit and said splitter connector directs flow from said outlet conduit.

22. The auto-cleaning and auto-zeroing system as claimed in claim 19, wherein one of said modes is a cleaning (ionization) cycle, wherein said splitter connector directs flow from said bypass conduit.

23. The auto-cleaning and auto-zeroing system as claimed in claim 22, wherein said valve directs flow from said first conduit.

24. The auto-cleaning and auto-zeroing system as claimed in claim 19, wherein the system continuously performs a measurement cycle, followed by a cleaning (flushing) cycle and a cleaning (ionization) cycle.

25. The auto-cleaning and auto-zeroing system as claimed in claim 1, wherein said valve is a 4/2 valve.

* * * * *